US007706993B2

(12) United States Patent
Teshima (10) Patent No.: US 7,706,993 B2
(45) Date of Patent: Apr. 27, 2010

(54) METHOD AND PROGRAM FOR CORRECTING PEAK POSITION OF SPECTRUM WAVEFORM PATTERN

(75) Inventor: Shoichi Teshima, Kitahiroshima (JP)

(73) Assignee: Angletry Associates, Kitahiroshima-shi (JP)

( * ) Notice: Subject to any disclaimer, the term of this patent is extended or adjusted under 35 U.S.C. 154(b) by 854 days.

(21) Appl. No.: 11/552,685

(22) Filed: Oct. 25, 2006

(65) Prior Publication Data

US 2007/0110144 A1 May 17, 2007

(30) Foreign Application Priority Data

Nov. 11, 2005 (JP) ............................. 2005-327230

(51) Int. Cl.
*G01R 13/00* (2006.01)
*G01N 37/00* (2006.01)
(52) U.S. Cl. .............................. 702/66; 702/76; 702/81; 702/84
(58) Field of Classification Search .............. 702/62–84
See application file for complete search history.

(56) References Cited

U.S. PATENT DOCUMENTS

| 4,353,242 | A | * | 10/1982 | Harris et al. ................ 73/23.36 |
| 5,969,228 | A | * | 10/1999 | Gorenstein ................. 73/23.22 |
| 2005/0021262 | A1 | * | 1/2005 | Mantyla et al. .............. 702/76 |

FOREIGN PATENT DOCUMENTS

JP         2004-110602 A     4/2004

OTHER PUBLICATIONS

Yi-Zeng Liang et al., Quality control of herbal medicines, Journal of Chromatography B, 812, 2004, pp. 53-70.
Li-Wei Yang et al., Fingerprint quality control of Tianjihuang by high-performance liquid chromatography-photodiode array detection, Journal of Chromatography A, 1070, 2005, pp. 35-42.
A.M. Van Nederkassel et al., A comparison of three algorithms for chromatograms alignment, Journal of Chromatography A, 1118, 2006, pp. 199-210.
Fan Gong et al., Information theory applied to chromatography fingerprint of herbal medicine for quality control, Journal of Chromatography A, 1002, 2003, pp. 25-40.
Bo-Yan Li et al., Spectral correlative chromatography and its application to analysis of chromatographic fingerprints of herbal medicine, J. Sep. Sci., 27, 2004, pp. 581-588.

* cited by examiner

*Primary Examiner*—Eliseo Ramos Feliciano
*Assistant Examiner*—Phuong Huynh
(74) *Attorney, Agent, or Firm*—Griffin & Szipl, P.C.

(57) ABSTRACT

The invention relates to a peak position correcting method that is a pre-process for testing whether properties of a product, a raw material, etc., are good or defective from a spectrum waveform pattern. The method involves setting a reference peak position in a single region including a spectrum waveform pattern, or setting reference peak positions in each of a plurality of regions; specifying a peak to be corrected as an object of correction in the single region or each of the plurality of regions; shifting the peak to be corrected to the reference peak position in the single region or in each of the plurality of regions; and substantially proportionally expanding or contracting the spectrum waveform pattern positioned at both sides of the peak to be corrected in the horizontal axis direction.

4 Claims, 6 Drawing Sheets

| X | Y |
|---|---|
| 1 | 20,677 |
| 2 | 19,416 |
| 3 | 18,080 |
| 4 | 16,802 |
| 5 | 15,576 |
| 6 | 14,510 |
| 7 | 13,562 |
| 8 | 12,780 |
| 9 | 12,108 |
| 10 | 11,554 |
| 11 | 11,089 |
| 12 | 10,706 |
| 13 | 10,387 |
| 14 | 10,117 |
| 15 | 9,887 |
| 16 | 9,704 |
| 17 | 9,550 |
| 18 | 9,423 |
| 19 | 9,315 |
| 20 | 9,230 |
| 21 | 9,160 |
| 22 | 9,099 |
| 23 | 9,051 |
| 24 | 9,021 |
| 25 | 9,019 |
| 26 | 9,015 |
| 27 | 9,017 |
| 28 | 9,069 |
| 29 | 9,128 |
| 30 | 9,202 |
| 31 | 9,305 |
| 32 | 9,446 |
| 33 | 9,617 |
| 34 | 9,849 |
| 35 | 10,100 |
| 36 | 10,368 |
| 37 | 10,654 |
| 38 | 10,918 |
| 39 | 11,185 |
| 40 | 11,462 |
| 41 | 11,724 |
| 42 | 11,996 |
| 43 | 12,268 |
| 44 | 12,585 |
| 45 | 12,959 |
| 46 | 13,364 |
| 47 | 13,854 |
| 48 | 14,391 |
| 49 | 15,025 |
| 50 | 15,703 |
| 51 | 16,427 |
| 52 | 17,139 |
| 53 | 17,767 |
| 54 | 18,343 |
| 55 | 18,780 |
| 56 | 19,179 |
| 57 | 19,624 |
| 58 | 20,212 |
| 59 | 21,143 |
| 60 | 22,510 |
| 61 | 24,468 |
| 62 | 27,049 |
| 63 | 30,490 |
| 64 | 34,831 |
| 65 | 40,391 |
| 66 | 47,619 |
| 67 | 56,959 |
| 68 | 69,145 |
| 69 | 84,815 |
| 70 | 104,776 |
| 71 | 129,149 |
| 72 | 157,767 |
| 73 | 189,199 |
| 74 | 221,620 |
| 75 | 252,122 |
| 76 | 279,133 |
| 77 | 300,728 |
| 78 | 317,404 |
| 79 | 330,275 |
| 80 | 342,338 |
| 81 | 356,538 |
| 82 | 377,176 |
| 83 | 406,356 |
| 84 | 446,106 |
| 85 | 491,675 |
| 86 | 537,096 |
| 87 | 569,428 |
| 88 | 578,344 |

FIG. 3A

| X' | ORIGINAL X | Y |
|---|---|---|
| 1 | 1 | 20,677 |
| 2 | 2 | 19,416 |
| 3 | 3 | 18,080 |
| 4 | 5 | 15,576 |
| 5 | 6 | 14,510 |
| 6 | 7 | 13,562 |
| 7 | 8 | 12,780 |
| 8 | 10 | 11,554 |
| 9 | 11 | 11,089 |
| 10 | 12 | 10,706 |
| 11 | 13 | 10,387 |
| 12 | 15 | 9,887 |
| 13 | 16 | 9,704 |
| 14 | 17 | 9,550 |
| 15 | 18 | 9,423 |
| 16 | 20 | 9,230 |
| 17 | 21 | 9,160 |
| 18 | 22 | 9,099 |
| 19 | 23 | 9,051 |
| 20 | 25 | 9,019 |
| 21 | 26 | 9,015 |
| 22 | 27 | 9,017 |
| 23 | 28 | 9,069 |
| 24 | 30 | 9,202 |
| 25 | 31 | 9,305 |
| 26 | 32 | 9,446 |
| 27 | 33 | 9,617 |
| 28 | 35 | 10,100 |
| 29 | 36 | 10,368 |
| 30 | 37 | 10,654 |
| 31 | 38 | 10,918 |
| 32 | 40 | 11,462 |
| 33 | 41 | 11,724 |
| 34 | 42 | 11,996 |
| 35 | 44 | 12,585 |
| 36 | 45 | 12,959 |
| 37 | 46 | 13,364 |
| 38 | 47 | 13,854 |
| 39 | 49 | 15,025 |
| 40 | 50 | 15,703 |
| 41 | 51 | 16,427 |
| 42 | 52 | 17,139 |
| 43 | 54 | 18,343 |
| 44 | 55 | 18,780 |
| 45 | 56 | 19,179 |
| 46 | 57 | 19,624 |
| 47 | 59 | 21,143 |
| 48 | 60 | 22,510 |
| 49 | 61 | 24,468 |
| 50 | 62 | 27,049 |
| 51 | 64 | 34,831 |
| 52 | 65 | 40,391 |
| 53 | 66 | 47,619 |
| 54 | 67 | 56,959 |
| 55 | 69 | 84,815 |
| 56 | 70 | 104,776 |
| 57 | 71 | 129,149 |
| 58 | 72 | 157,767 |
| 59 | 74 | 221,620 |
| 60 | 75 | 252,122 |
| 61 | 76 | 279,133 |
| 62 | 77 | 300,728 |
| 63 | 79 | 330,275 |
| 64 | 80 | 342,338 |
| 65 | 81 | 356,538 |
| 66 | 82 | 377,176 |
| 67 | 84 | 446,106 |
| 68 | 85 | 491,675 |
| 69 | 86 | 537,096 |
| 70 | 88 | 578,344 |

METHOD AND PROGRAM FOR CORRECTING PEAK POSITION OF SPECTRUM WAVEFORM PATTERN

This application claims priority from Japan Patent Application No. 2005-327230, filed Nov. 11, 2005, the entire disclosure of which is incorporated herein by reference.

BACKGROUND OF THE INVENTION

1. Field of the Invention

The present invention relates to a method and a program for correcting a peak position as preprocessing for testing of whether a product, etc., is good or defective from a spectrum waveform pattern thereof.

2. Description of the Related Art

Figure 7A:
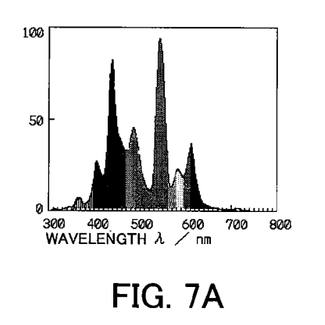
FIGS. 7A and 7B depict examples of the spectrum waveform of a fluorescent lamp.
Figure 7B:
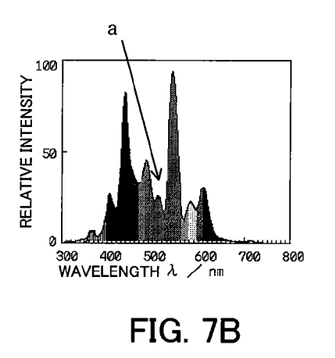
Figure 8:
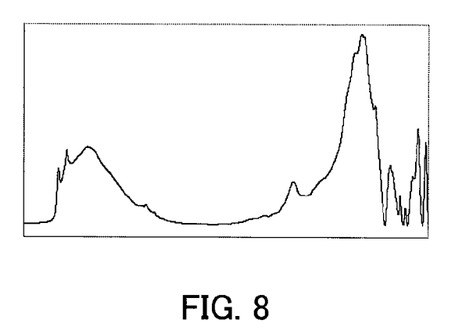
FIG. 8 depicts an example of the spectrum waveform obtained as a result of measuring herb medicine materials, etc. by using e.g., a chromatograph.

There exist a lot of products and materials capable of using a spectrum waveform for testing of whether the product is a good one or a defective one. For example, as shown in FIGS. 7A and 7B, a fluorescent tube has different energy intensities depending on wavelength so that the emission property can be expressed by the spectrum waveform. The properties of herb medicine materials, agricultural products, and petrochemical products can also be expressed as spectrum waveforms by using a chromatograph or an infrared spectrometer, as shown in FIG. 8.

In this manner, in the industry field or in the fields of chemicals, agriculture, etc., the spectrum waveform is widely used for testing of properties of products and raw materials/ingredients. In every field, the spectrum waveform of a product to be tested is compared with the spectrum waveform group that was judged as a good product in the past to judge whether it can be regarded as the same. For example, supposing the waveform shown in FIG. 7A is a typical spectrum judged as a good product in the past, the same waveform pattern is regarded to appear in substantially every portions in FIG. 7B. However, the mountain figure of the wave pattern indicated by the arrow of FIG. 7A has a difference from the wave pattern of FIG. 7B, thus generating question about identities of spectrum waveforms.

At the same time, there exist substantively no just the same spectrum waveforms. More specifically, there exist no same spectrum waveforms which are completely coincident with each other both in the vertical axis direction and horizontal axis direction. Differences are present among individuals even in good products. A completely coincident waveform pattern cannot be acquired even when the same object is measured by the same measuring equipment. One reason is the presence of various errors such as an error among individuals to be measured, a variance in the properties of the object itself, and a measurement error inherent to the measuring equipment. These errors occurs in both directions of the vertical axis and horizontal axis.

As described above, although there exist no just the same spectrum waveforms, testing of products by use of a spectrum waveform, that is, judgment of degree of similarity of spectrum waveforms is carried out. Thus, an error especially in the horizontal axis direction often becomes problematic in the testing process. The reason is that, when comparing the spectrum waveforms, if peaks and irregularity positions are level in the horizontal axis direction, the testing can easily be performed by focusing on only the difference in the vertical axis direction.

A measurement result by chromatograph is one example of easy occurrence of errors of the spectrum waveform in the horizontal axis direction. The chromatograph easily causes an error in the horizontal axis direction due to its measurement principle so that when the same testing object is measured more than once, the same peak in the horizontal axis direction may appear in the range of several percentages of the whole horizontal width of the spectrum waveform. Therefore, as for the peak position correction especially for the chromatograph, studies using a statistical approach and the like have been carried out. In the other spectrum waveforms, even though there is some difference, occurrence of an error is inevitable. Accordingly, peak position correction has become an important problem in the visual testing or computer-based automatic testing since the error highly affects the testing accuracy.

Figure 5A:
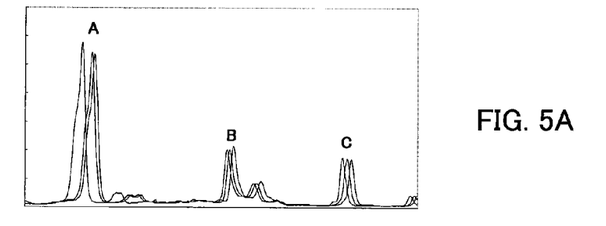
FIGS. 5A and 5B depict three spectrum waveforms before and after, respectively, subjected to peak position correction.
Figure 5B:
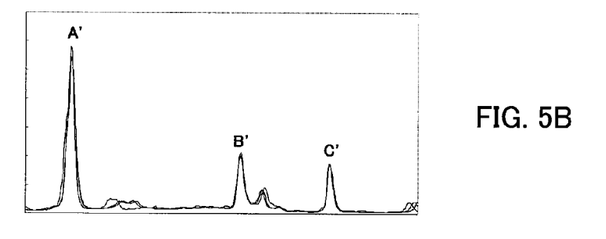

An example of a peak position error of a spectrum waveform is shown in FIG. 5B. FIG. 5B shows three different object spectrum waveforms having the same properties. In the diagram, positions of "peak A", "peak B", and "peak C" which express properties of materials are different in the horizontal axis direction. The difference may be caused by errors owing to the above various parameters. These three different spectrum waveforms have nonlinear errors in the horizontal axis direction. More specifically, the error does not occur in the form of mere translation or even expansion and contraction in the horizontal axis direction, but nonuniformly fluctuates depending on the place.

Consequently, it is highly required as preprocessing of the testing to perform the error correction in the horizontal axis direction, i.e., peak position correction with high accuracy (in other words, to match as much as possible the positions in the horizontal axis direction of fellow peaks to be regarded as the same peak as for a plurality of peak positions of the spectrum waveform). In addition, the peak position correction must be performed not only in high accuracy but also as rapidly as possible. Especially recently, a development for performing the test processing with a computer has been advanced and a development of an elemental technology to be required has been performed (for example, see the method described in commonly assigned Japanese Patent Application Laid-Open Publication No. 2004-110602 according to development by the inventor). When testing process is performed by a computer, a peak position correcting method becomes essential in particular. The reason is that peaks can flexibly be associated in case of visual checks, but that judging the accuracy would extremely deteriorate if the corresponding peaks are not properly specified in case of computers.

Hitherto-applied typical methods of the peak position correction are as follows.

Figure 9A:
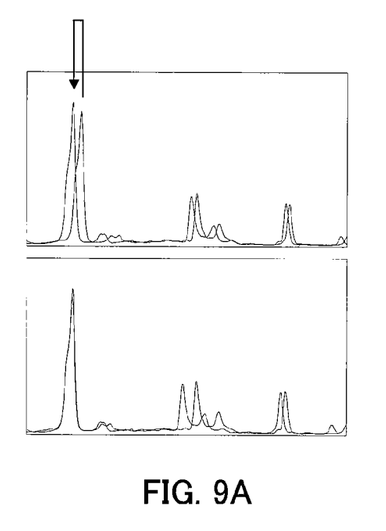
FIGS. 9A and 9B depict examples of the conventional peak position correcting method.

(1) A method of selecting one typical peak from a spectrum waveform and adjusting another spectrum to the selected typical peak in the horizontal axis position (see FIG. 9A).

This method is effectively applied when the spectrum waveform uniformly shifts in the horizontal axis direction. The more the selected typical peak is positioned in substantially center of the spectrum waveform in the horizontal axis direction, the more error correction at both ends may fairly be performed.

Figure 9B:
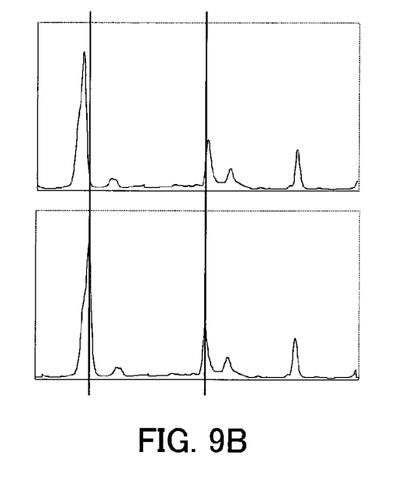

(2) A method of preparing a sample having one or a plurality of ingredients whose peak appearance positions in the horizontal axis direction are known, measuring the sample, and correcting the corresponding peak positions appearing in the testing object relative to the appearing peeks (see FIG. 9B).

The two vertical lines described in FIG. 9B designate the peak appearance positions of the known ingredients. When two ingredients are used, corresponding peaks of the spectrum waveform to be tested are adjusted to the two peak positions and the waveform therebetween is expanded or contracted in a linear processing manner. The method of using peak appearance position of the known ingredient is a method generally used in a chromatograph, etc., and is called "internal standard". Error in the horizontal axis direction of spectrum waveform generally involves expansion and contraction, so that using two peaks provides better effect in peak position correction.

Figure 10:
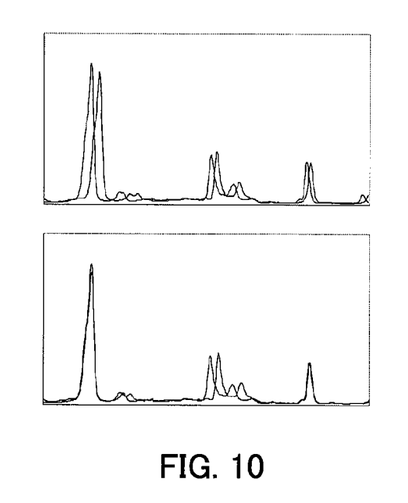
FIG. 10 depicts other examples of the conventional peak position correcting method.

(3) A method of selecting two typical peaks from among peaks of a spectrum waveform defined as a standard and correcting the corresponding peaks of another spectrum waveform at the typical peak positions (see FIG. 10).

In the example shown in FIG. 10, the right and left two peaks are selected and the spectrum waveform existing between the peaks is expanded or contracted in a linear processing manner. In general, by selecting peaks nearer to both ends as far as possible, correction effectiveness may be improved. The method is, for example, described in the specification of U.S. Pat. No. 5,969,228. A different point from the above described internal standard method is no need for separately preparing samples.

In the above methods (1) and (2), however, the number of peaks set or selected as a correcting standard are about two and a peak position existing between the peaks is merely expanded or contracted in the proportional manner to be corrected. That is, there exists a problem in that the methods are unavailable for a spectrum waveform which is expanded or contracted in a nonlinear manner though available for a spectrum waveform which is expanded or contracted in the proportional manner.

Particularly, in a chromatograph, etc., peak appearance positions are fluctuated in a nonlinear manner. For example, a peak may shift to the front and another peak may shift to the rear. In this case, the conventional methods involve problems in that correcting accuracy of peak position except correction reference peak may become extremely insufficient and that error of peak position may rather increase by the correction.

SUMMARY OF THE INVENTION

The present invention was conceived in the light of such circumstances and it is therefore the object of the present invention to provide a peak position correcting method and program for properly correcting a spectrum waveform even when the peak positions of the spectrum waveform have nonlinear fluctuations and errors.

In order to achieve the above object, according to an aspect of the present invention there is provided a peak position correcting method that is a preprocessing for carrying out a testing of whether properties of a product, a raw material, etc., are good or defective from a spectrum waveform pattern, the method comprising the steps of setting a reference peak position in a single region including a spectrum waveform pattern, or setting reference peak positions in each of a plurality of regions obtained by dividing the spectrum waveform pattern in a horizontal axis direction; specifying a peak to be corrected as an object of correction in the single region or each of the plurality of regions; shifting the peak to be corrected to the reference peak position in the single region or in each of the plurality of regions; and substantially proportionally expanding or contracting the spectrum waveform pattern positioned at both sides of the peak to be corrected in the horizontal axis direction, depending on the amount of the shifting, in the single region or in each of the plurality of regions.

Preferably, the step of specifying the peak to be corrected includes setting a predetermined range at both sides of the reference peak position in the horizontal axis direction and specifying the peak to be corrected from within the predetermined range.

In order to achieve the above object, according to another aspect of the present invention there is provided a peak position correcting program that is used in a preprocessing for carrying out a testing of whether properties of a product, a raw material, etc., are good or defective from a spectrum waveform pattern, the program operable to drive a computer to execute the steps of setting a reference peak position in a single region including a spectrum waveform pattern, or setting reference peak positions in each of a plurality of regions obtained by dividing the spectrum waveform pattern in a horizontal axis direction, and storing the set reference peak positions in a storage device; specifying a peak to be corrected as an object of correction in the single region or in each of the plurality of regions, and storing the specified peak in the storage device; shifting the peak to be corrected to the reference peak position in the single region or in each of the plurality of regions, and storing the shifted peak in the storage device; and substantially proportionally expanding or contracting the spectrum waveform pattern positioned at both sides of the peak to be corrected in the horizontal axis direction, depending on the amount of the shifting, in the single region or in each of the plurality of regions, and storing the substantially proportionally expanded or contracted spectrum waveform pattern in the storage device.

Preferably, the step of specifying the peak to be corrected includes setting a predetermined range at both sides of the reference peak position in the horizontal axis direction and specifying the peak to be corrected from within the predetermined range for storage in the storage device.

According to the method and program of the preset invention, the corresponding peaks can be corrected with high accuracy even when a spectrum waveform has nonlinear fluctuations and errors in the horizontal axis direction in the testing process using the spectrum waveform. This enables testing of whether products and raw materials/ingredients are good or defective with high accuracy.

BRIEF DESCRIPTION OF THE DRAWINGS

The above and other objects, aspects, features and advantages of the present invention will become more apparent from the following detailed description when taken in conjunction with the accompanying drawings, in which:

FIGS. 3A and 3B depict specific examples of numerical values in the peak position correcting method of the present invention;

DESCRIPTION OF THE PREFERRED EMBODIMENTS

Figure 1:
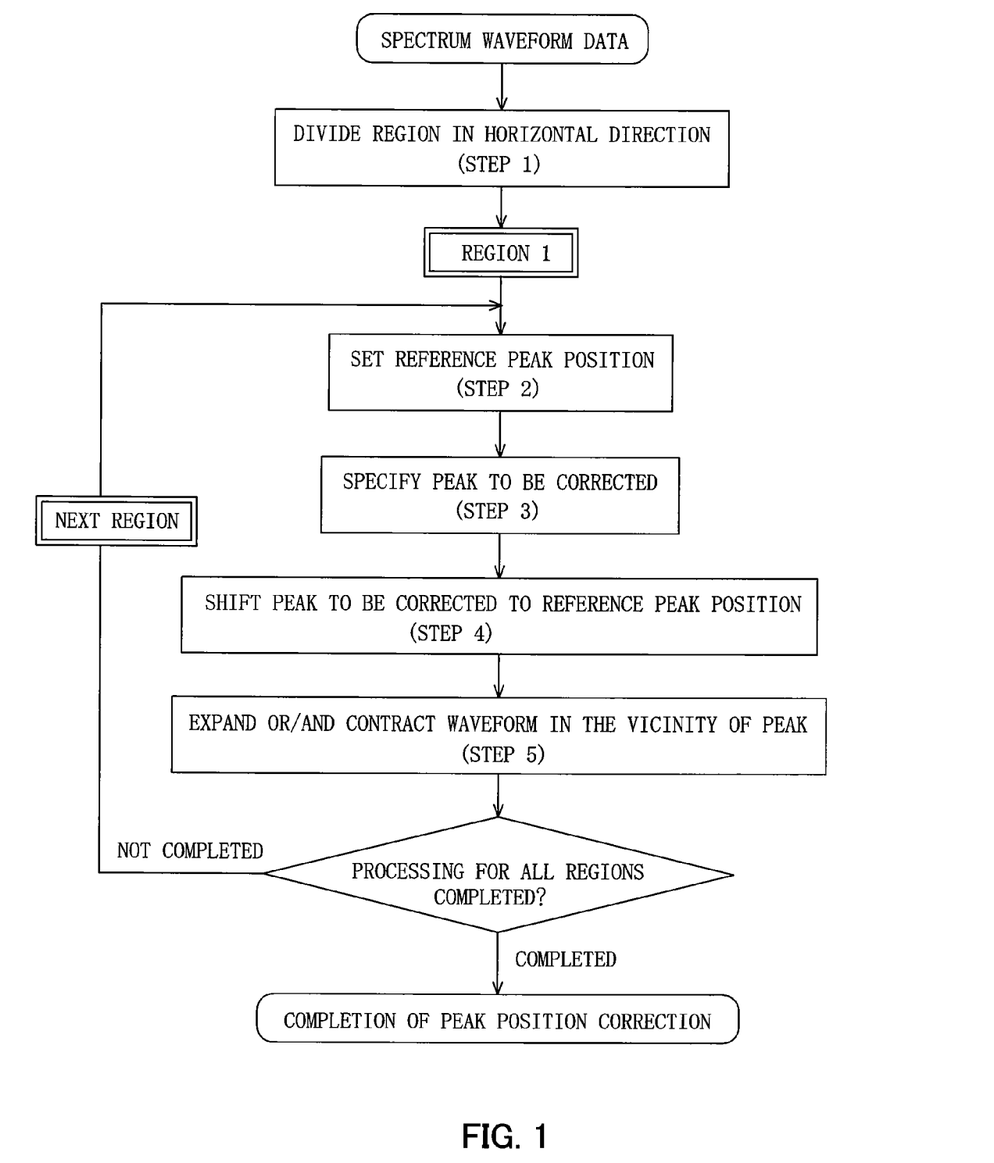
FIG. 1 is a flow diagram of a schematic configuration of a peak position correcting method according to a preferred embodiment of the present invention.
Figure 2:
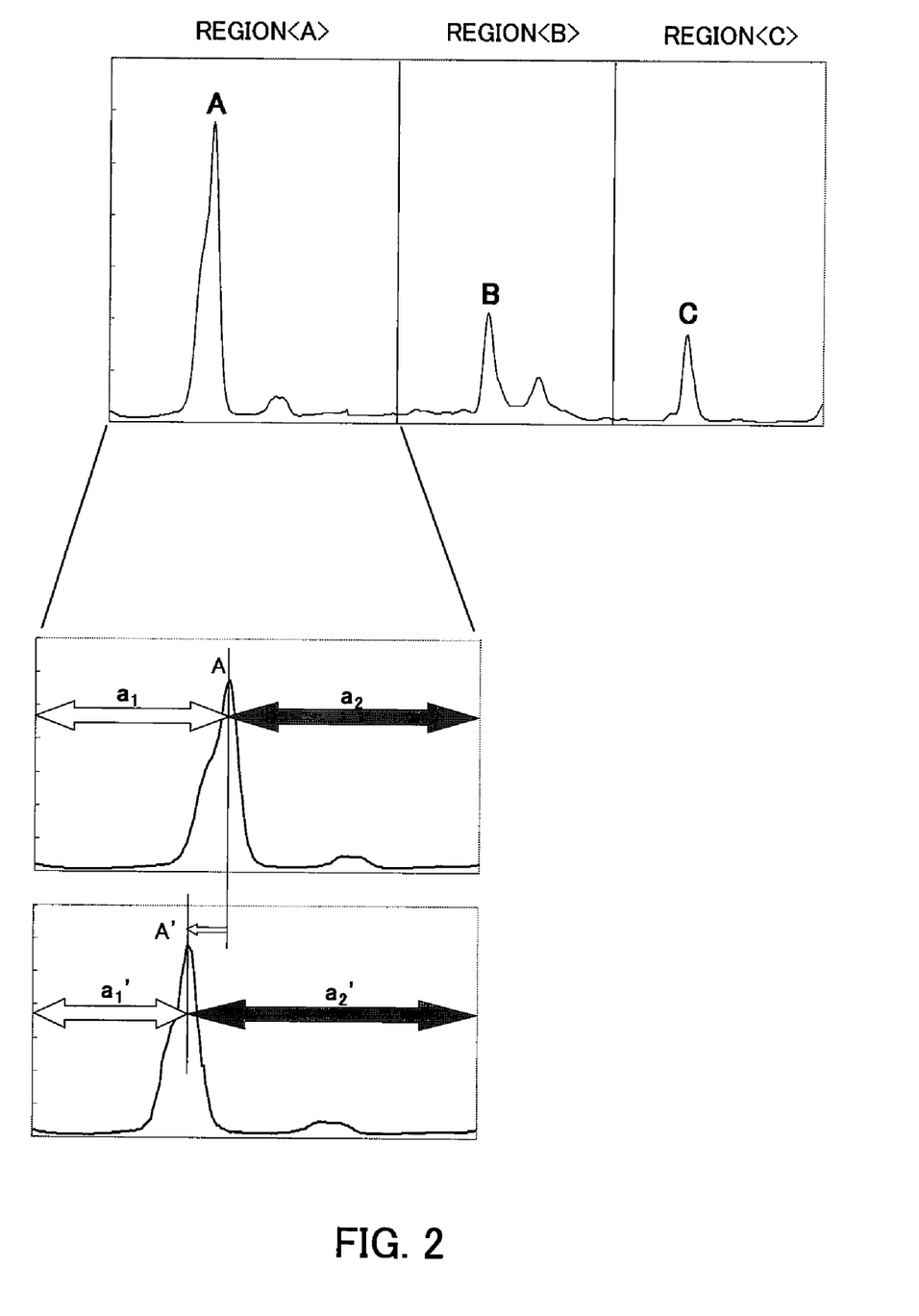
FIG. 2 is an explanatory view of region division, peak position shifting, etc, in the peak position correcting method of the present invention.

A peak position correcting method according to a preferred embodiment of the present invention will now be described in detail with reference to the drawings. FIG. 1 depicts schematic flow of a configuration of a peak position correcting method according to the preferred embodiment of the present invention. In the present embodiment, a spectrum waveform pattern shown in FIG. 2 is described as an example.

The spectrum waveform pattern is first divided into a plurality of regions in the horizontal axis direction (step 1). Various dividing methods are conceivable. In the present embodiment, the pattern is divided into regions that respectively have typical peaks A, B, and C from among the spectrum waveform and that are respectively referred to as region <A>, region <B>, and region <C>. As used herein, the typical peak is defined in general as an important peak, etc., indicative of properties of the object shown in the spectrum waveform, but is not limited to the definition.

A reference peak position A' is set as a target position of the peak position correction for region <A> from among the divided three regions (step 2). The reference peak position A' means "a position for the peak to originally appear", etc., from, e.g., the past data records. Note that the horizontal axis positions from the left and right ends of the typical peak A are designated at $a_1$ and $a_2$, respectively, and the horizontal axis positions from the left and right ends of typical peak A' are designated at $a_1'$ and $a_2'$ (therefore, as is apparent from FIG. 2, $a_1+a_2=a_1'+a_2'$).

A peak to be corrected is then specified (Step 3). In this example, the peak to be corrected is the typical peak A.

The horizontal axis position $a_1$ of the peak to be corrected (typical peak A) is shifted to the reference peak position A' (Step 4). To be more specific, in case of the example shown in FIG. 2, the reference peak position A' is positioned to the left hand of the typical peak A, so that the horizontal axis position $a_1$ of the typical peak A is shifted leftward by $a_1-a_1'$.

The spectrum waveform positioned to the right and left hands of the typical peak A is then expanded and contracted (Step 5). More specifically, the spectrum waveform positioned to the left hand of the typical peak A is contracted by $a_1'/a_1$ times and the spectrum waveform positioned at right hand thereof is expanded by $a_2'/a_2$ times.

An example of the specific method of Step 4 and Step 5 will be described. The coordinate in the horizontal axis direction of the region <A> may be X and left end position therein may be X=0. The coordinate in the vertical axis direction of the spectrum waveform at the coordinate X may be Y(X). In the region <A>, the coordinate X ranges from 0 to $(a_1+a_2)$.

The coordinate in the vertical axis direction of the spectrum waveform of the region having the reference peak position A' defined may be Y'(X).

The spectrum waveform Y(X) positioned to the left hand of the typical peak A is corrected to Y'(X) as follows.

$$Y'(X)=Y\times[X\times(a_1/a_1')] \quad (1)$$

The spectrum waveform Y(X) positioned to the right of the typical peak is corrected to Y'(X) as follows.

$$Y'(X)=Y\times[(X-a_1')\times(a_2/a_2')+a_1] \quad (2)$$

In general, X is an integer, so that integer processing is carried out in [ ] of the right side of equations (1) and (2).

By the above processes, the typical peak A is shifted to the reference peak position A' and the spectrum waveform except the typical peak is expanded or contracted for correction.

An example of specific numerical values is shown in FIGS. 3A and 3B. Referring to FIGS. 3A and 3B, actual numerical values are shown when the spectrum waveform having the horizontal axis ranging from 1 to $a_1$ is corrected (contracted in this example) to the spectrum waveform ranging from 1 to $a_1'$. That is, the spectrum waveform having the horizontal axis (X) coordinate ranging from 1 to 88 (see FIG. 3A) is contracted to the range of 1 to 70 in horizontal axis coordinate (see FIG. 3B). In FIG. 3B, the corresponding X coordinate before correction is represented as "original X". This shows that, for example, the value in line 10 (X=10) of FIG. 3A is shifted to line 8 of FIG. 3B after correction. In FIG. 3, correspondence relationship of before/after correction is shown by the arrows about every 10 lines.

By applying similar processing as effected on the region <A> to the remaining two regions (region <B> and region <C>), the peak position correction of the spectrum waveform is performed in all the regions.

Figure 4A:
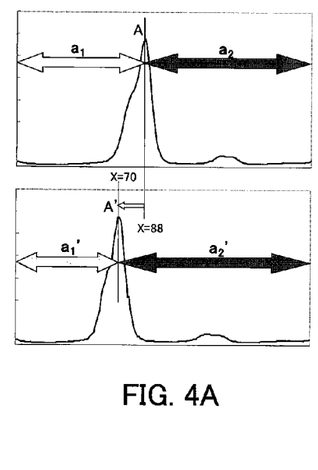
FIGS. 4A to 4C depict spectrum waveforms in regions after/before correction.
Figure 4B:
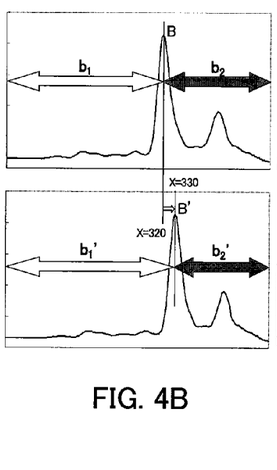
Figure 4C:
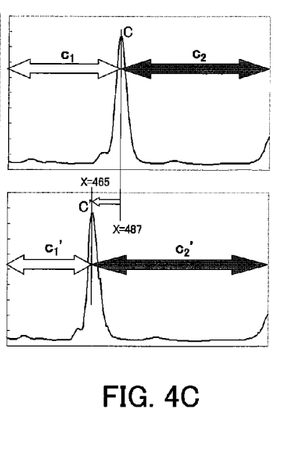

FIGS. 4A TO 4C depict spectrum waveforms in the regions <A>, <B>, and <C> of before/after correction. Referring to FIGS. 4A to 4C, the peak positions are shifted to the left in the region <A>, to the right in the region <B>, and to the left in the region <C> after correction. Such differences in the correction direction of the peak positions represent that the peak positions fluctuate in a nonlinear manner.

In this manner, errors of peak positions of the spectrum waveform are corrected for each region.

FIGS. 5A and 5B depict three spectrum waveforms before and after, respectively, subjected to the peak position correction. Before the correction (see FIG. 5A), the peaks A, B, and C scatter in a nonlinear manner. After the correction, matching of the peaks is apparent (see FIG. 5B). Errors remain in the portions except peaks but a reduction of errors is visible. The errors can be minimized in the error remaining portions as well by increasing the number of divided regions Other than the method of defining the reference peak position based on the past data records as described above, various methods are conceivable such as a method of selecting one spectrum waveform considered as a typical one and regarding the peak group thereof as a reference.

The typical peak in each region may generally be the most high peak. However, this is not limitative and any peak may be employed as long as the peak can be specified as a peak. For example, there exists a somewhat low peak to the right of the peak B in the region <B> of FIG. 3. When the somewhat low peak is a technically more important peak than peak B, the somewhat low peak may be selected as a typical peak instead of the peak B.

A method of specifying a peak to be corrected will then be described. When the peak position is corrected, a peak to be corrected needs to be specified as described above. In the example shown in FIGS. 3A and 3B where the typical peak is the peak to be corrected, specifying the peaks A, B, and C is relatively easy. However, in the case e.g., where another peak exists near the peak, a wrong peak may be identified. Even when a typical peak exists in an object region, the peak may originally present different properties. In this case, specifying the peak as a peak to be corrected is inappropriate. Therefore, when the typical peak A is away more than the allowable range from the position of the reference peak A' in the horizontal axis direction, the typical peak A may not be corrected to the peak A'.

Figure 6A:
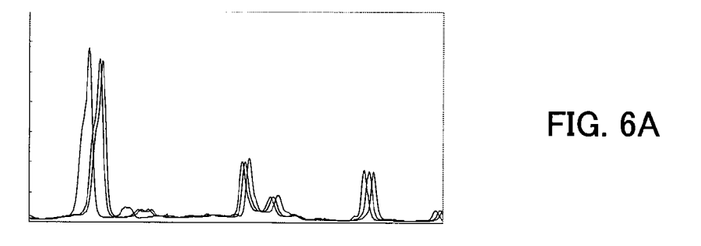
FIGS. 6A and 6B are explanatory views of a method of selecting a peak to be corrected from within a predetermined acceptable range in the peak position correcting method of the present invention.
Figure 6B:
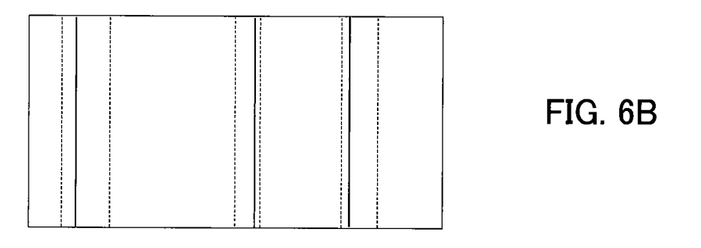

Consequently, it is preferred, in such a case, that the peak to be corrected be selected from within a proper allowable range. For example, when correcting the three peak positions of the spectrum waveforms shown in FIG. 6A, peaks to be corrected are specified from within the range shown by the dotted line in FIG. 6B. The range shown by the dotted line is set in consideration of, for example, measuring errors, variations between individuals, etc. If selectable peaks are not present within the range, then, the spectrum waveform is processed as a "correction impossible" waveform.

A program for causing a computer to execute the above steps (i.e., steps 1 to 5) will be described. The computer executing the present program may include a CPU (central processing unit), a storage device such as a memory, and a hard disc, an input device such as a key board, a display, and an output device (all not shown) which are mutually connected by a bus, or may be a microchip-type processing unit, etc.

At first, a spectrum waveform pattern inputted by the input device is stored in the memory. Next, the spectrum wave pattern is divided into a plurality of regions in the horizontal axis direction for storage in the memory. Next, reference peak positions are set in each region for storage in the memory. Next, peak to be corrected are specified in each region to be stored in the memory. Next, the peaks to be corrected are shifted to the reference peak positions in each region, to be stored in the memory. Next, the spectrum waveform patterns positioned at both sides of the peak to be corrected are substantially proportionally expanded or contracted in the horizontal axis direction depending on the amount of the shifting in each region to be stored in the memory.

Although in the above described example, data is stored in the memory, data is stored in a large-capacity storage device such as a hard disk when the data is heavy.

The present invention is not limited to the above embodiment and can variously be changed or modified without departing from the scope of the present invention as defined in claims. Needless to say, these are encompassed within the scope of the present invention.

For example, although in the above embodiment, the spectrum waveform pattern is divided into a plurality of regions in the horizontal axis direction for the peak position correction in each region, the peak position correction may be effected by the similar processes to the above except the region dividing step in a single region including the spectrum waveform pattern.

What is claimed is:

1. A peak position correcting method that is a preprocessing for carrying out a testing of whether properties of a product, a raw material, etc., are good or defective from a spectrum waveform pattern, the method comprising the steps of:
setting a reference peak position in a single region including a spectrum waveform pattern, or setting reference peak positions in each of a plurality of regions obtained by dividing the spectrum waveform pattern in a horizontal axis direction;
specifying a peak to be corrected as an object of correction in the single region or each of the plurality of regions;
shifting the peak to be corrected to the reference peak position in the single region or in each of the plurality of regions; and
using a computer, substantially proportionally expanding or contracting the spectrum waveform pattern positioned at both sides of the peak to be corrected in the horizontal axis direction, depending on the amount of the shifting, in the single region or in each of the plurality of regions.

2. The method of claim 1, wherein
the step of specifying the peak to be corrected includes setting a predetermined range at both sides of the reference peak position in the horizontal axis direction and specifying the peak to be corrected from within the predetermined range.

3. A peak position correcting program, stored on a computer readable medium, that is used in a preprocessing for carrying out a testing of whether properties of a product, a raw material, etc., are good or defective from a spectrum waveform pattern, wherein the program is operable to drive a computer to execute the steps of:
setting a reference peak position in a single region including a spectrum waveform pattern, or setting reference peak positions in each of a plurality of regions obtained by dividing the spectrum waveform pattern in a horizontal axis direction, and storing the set reference peak positions in a storage device;
specifying a peak to be corrected as an object of correction in the single region or in each of the plurality of regions, and storing the specified peak in the storage device;
shifting the peak to be corrected to the reference peak position in the single region or in each of the plurality of regions, and storing the shifted peak in the storage device; and
substantially proportionally expanding or contracting the spectrum waveform pattern positioned at both sides of the peak to be corrected in the horizontal axis direction, depending on the amount of the shifting, in the single region or in each of the plurality of regions, and storing the substantially proportionally expanded or contracted spectrum waveform pattern in the storage device.

4. The program of claim 3, wherein
the step of specifying the peak to be corrected includes setting a predetermined range at both sides of the reference peak position in the horizontal axis direction and specifying the peak to be corrected from within the predetermined range for storage in the storage device.

* * * * *